United States Patent
Wang et al.

(10) Patent No.: US 6,807,250 B2
(45) Date of Patent: Oct. 19, 2004

(54) COLLIMATION DEVICE AND METHOD FOR ACQUIRING A RADIATION IMAGE OF A LONG BODY PART USING DIRECT DIGITAL X-RAY DETECTORS

(75) Inventors: Xiaohui Wang, Pittsford, NY (US); David H. Foos, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 446 days.

(21) Appl. No.: 09/845,587

(22) Filed: Apr. 30, 2001

(65) Prior Publication Data

US 2002/0191750 A1 Dec. 19, 2002

(51) Int. Cl.⁷ .............................................. G01N 23/04
(52) U.S. Cl. ............................................................ 378/63
(58) Field of Search .............................. 378/62, 63, 64, 378/65, 204, 205, 206, 207, 54–56

(56) References Cited

U.S. PATENT DOCUMENTS 5,005,196 A * 4/1991 Lanza et al. ................. 378/207
5,825,845 A * 10/1998 Blair et al. .................... 378/62

FOREIGN PATENT DOCUMENTS

DE     3825703 A1    2/1990

* cited by examiner

Primary Examiner—William Oen
(74) Attorney, Agent, or Firm—William F. Noval

(57) ABSTRACT

A method for acquiring a radiographic image of an elongated object, comprising: positioning an elongated object between a source of x-rays and a digital image capture device having an imaging dimension which is less than a like dimension of said elongated object; wherein said image source is stationary and said source projects an x-ray pattern which encompasses said elongated object; moving said digital image capture device in a direction parallel to said known imaging dimension to sequential contiguous stationary positions to acquire a sequence of radiographic images of said elongated object; and moving an assembly of x-ray opaque material which is positioned between said source of x-rays and said elongated object, and which has an opening for allowing passage of x-rays, such that said opening is synchronized with the movement of said digital image capture device to facilitate acquisition of said sequence of radiographic images at said stationary positions.

15 Claims, 4 Drawing Sheets

COLLIMATION DEVICE AND METHOD FOR ACQUIRING A RADIATION IMAGE OF A LONG BODY PART USING DIRECT DIGITAL X-RAY DETECTORS

FIELD OF THE INVENTION

This invention relates to digital radiography, and in particular to the imaging of a long human body part, such as the spine or the legs, using direct digital x-ray detector system.

BACKGROUND OF THE INVENTION

When a long segment of the human body is imaged using a conventional screen-film technique, special cassettes and films of extended length are used, such as 30×90 cm and 35×105 cm. As shown in FIG. 1, both the x-ray tube 101 and the cassette 103 are kept stationary during the exam, an image of the patient is acquired in a single exposure. As medical institutions are migrating from analog screen-film systems to digital modalities, such as flat-panel detector based digital radiography (DR) systems, this type of exam imposes a significant challenge. This is because the sizes of digital detectors are limited by cost and technology. The largest flat panel DR plates available today are limited to 43×43 cm. A detector of this size is capable of imaging only a portion of the body part at a time and thus is inadequate for performing imaging exams of longer length body parts such as the full spine or full leg. To address this problem, multiple exposures at varying patient positions must be acquired with the assumption that the patient can keep still during the exam. The individual images are then stitched together to reconstruct a larger composite image (see: U.S. Pat. Nos. 5,123,056 and 4,613,983). FIG. 2A shows the most commonly used approach with the DR systems. First, the patient 200 is exposed at a first position defined by the x-ray tube position 201 and the detector position 203. The collimator of the x-ray tube is adjusted such that the x-rays 202 can barely cover the detector while protecting the patient from unnecessary radiation in the non-imaging related regions. Second, after both the x-ray tube and the detector are translated parallel along axis 210 and 211 to a second position, as indicated by 206 and 208, a second exposure of the patient is conducted. There can be a slight overlap between the consecutive detector coverage in order to facilitate image stitching. This process can be continued until the full length of the body part to be examined is imaged. However, this stereovision-like image acquisition geometry has two major drawbacks: (1) mechanical complexity because both the detector and the x-ray tube need to be translated, and (2) inherent geometric distortion that makes precise image stitching almost impossible. As shown in FIG. 2B, if an object AB is situated in both the exposure coverage of x-ray tube position 201 and 206, it will be imaged at the corresponding detector position as $AB_0$ and $AB_1$, respectively, due to the divergence of the x-rays. With $AB_0$ pointing downward but $AB_a$ pointing upward, the same object has apparently created two different images. Evidently, $AB_0$ and $AB_1$ can not be registered together in the stitched image. Therefore, theoretically the images acquired at different tube positions can never be seamlessly and precisely stitched. This severity of this problem becomes worse if the body part get thicker. There is a need to develop an imaging method with DR that not only is simple in design but also can provide distortion-free images for stitching.

SUMMARY OF THE INVENTION

According to the present invention, there is provided a solution to the problems and a fulfillment of these needs.

According to a feature of the present invention, there is provided a method for acquiring a radiographic image of an elongated object, comprising: positioning an elongated object between a source of x-rays and a digital image capture device having an imaging dimension which is less than a like dimension of said elongated object; wherein said image source is stationary and said source projects an x-ray pattern which encompasses said elongated object; moving said digital image capture device in a direction parallel to said known imaging dimension to sequential contiguous stationary positions to acquire a sequence of radiographic images of said elongated object; and moving an assembly of x-ray opaque material which is positioned between said source of x-rays and said elongated object, and which has an opening for allowing passage of x-rays, such that said opening is synchronized with the movement of said digital image capture device to facilitate acquisition of said sequence of radiographic images at said stationary positions.

ADVANTAGEOUS EFFECT OF THE INVENTION

The invention has the following advantages.

1. The new method eliminates the stereovision-like geometric distortion caused by the current imaging method with DR systems, and allows precise registration of the partial images to reconstruct a larger composite image.

DETAILED DESCRIPTION OF THE INVENTION

Figure 1:
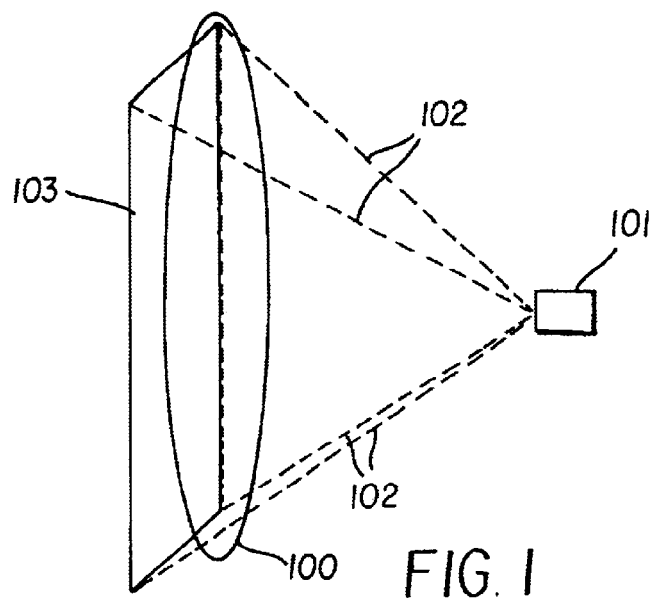
FIG. 1 is a diagrammatic view showing an imaging method used with screen-film systems.
Figure 2A:
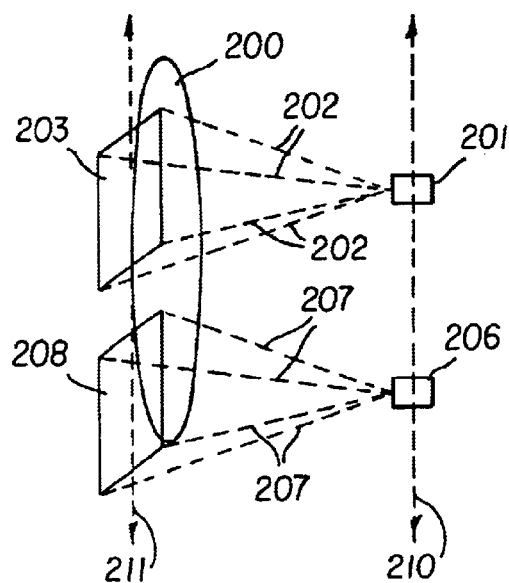
FIGS. 2A and 2B are diagrammatic views showing a method used with DR systems and the distortion introduced by the stereovision-like effect from the two subsequent exposures.
Figure 2B:
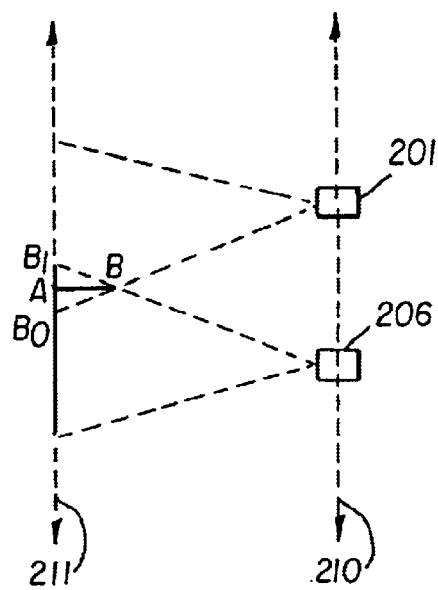
Figure 3A:
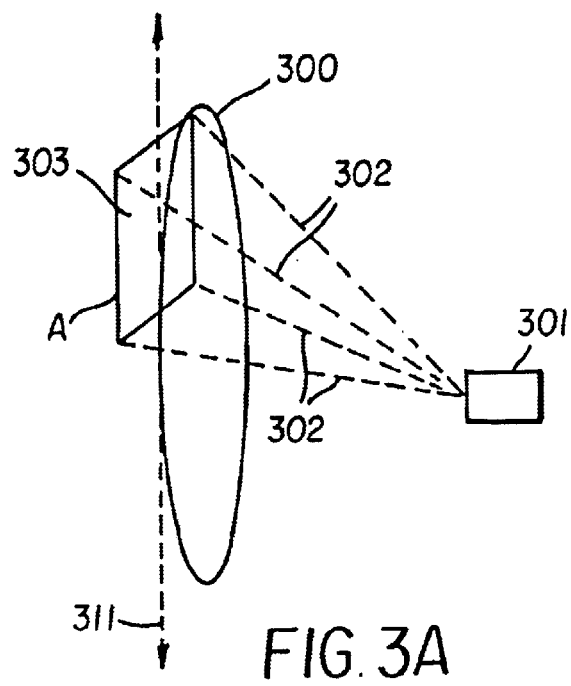
FIGS. 3A, 3B are diagrammatic views illustrating the invention with DR systems that allows multiple partial images to be taken with similar acquisition geometry to that obtained using screen-film systems.
Figure 3B:
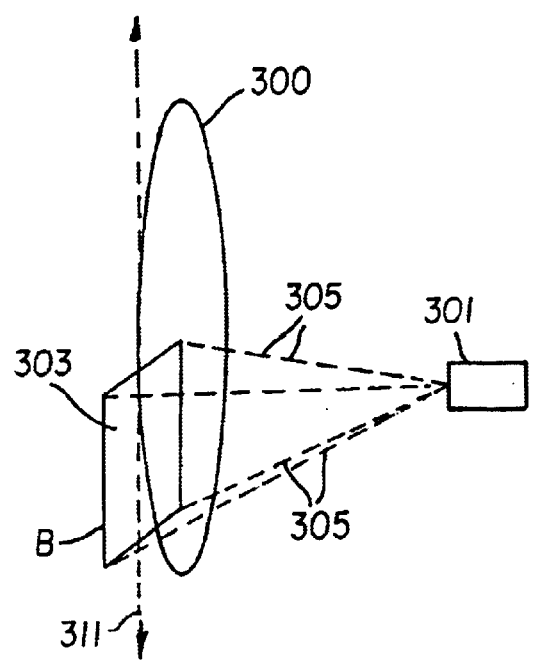

Referring now to FIGS. 3–6, the present invention will be described. FIGS. 3A and 3B show a radiographic imaging system incorporating the present invention.

The detector 303 of an digital image capture device can translate along axis 311 freely to various positions, but x-ray tube 301 is fixed in position and orientation during all exposures. First, the patient 300 is exposed at a first position defined by the detector position 303, position A. The collimator (see below) of the x-ray tube 301 is adjusted such that the x-rays 302 just cover the detector 303 for imaging. Second, after the detector 303 is translated to a second position as indicated by B, and the collimator is adjusted accordingly to allow only the imaging relevant x-rays 305 to arrive at the detector 303. A second exposure of the patient is then performed. This process can be continued until the full length of the body part to be examined is imaged. There can be a slight overlap between the consecutive detector coverage in order to facilitate image stitching. In doing so, the image acquisition geometry used by the conventional screen-film is emulated. The resultant stitched composite image can achieve the equivalent image quality in terms of image appearance and geometric precision.

Figure 4:
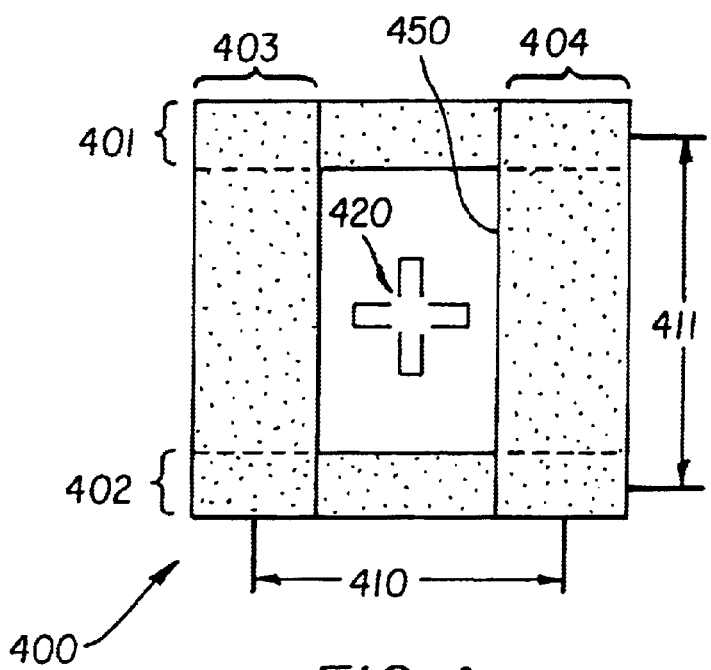
FIG. 4 is a diagrammatic view showing the movement of four collimation blades around the exposure field center cross marker in a conventional collimator.

The imaging method proposed in the present invention can not be implemented with a conventional x-ray collimator. FIG. 4 shows a construction diagram of the conventional collimator 400, which consists of two pairs of blades, top blade 401, bottom blade 402, left blade 403, and right 404 which form an opening 450. The blades are made of x-ray opaque material, such as lead, to gate the x-rays emitting from the x-ray tube through opening 450. Blades 401 and 402 always move synchronously in the opposite direction as indicated by arrow 410, blades 403 and 404 move in a similar way but in the direction indicated by arrow 411. Together the four blades create an adjustable rectangular aperture that is concentric with the central x-ray beam, which goes through the exposure field center cross marker 420. When a screen-film system is used, the x-ray tube and collimator are positioned such that the central x-ray beam is aimed towards the center of the body part to be examined and the collimator aperture is adjusted such that the x-ray beam covers the entire region to be imaged. However, this equipment configuration does not provide the flexibility for controlling the x-ray coverage for selectively imaging partial regions because the orientation and position of the x-ray tube and collimator are fixed.

The imaging method in the present invention can be implemented in a number of ways, such as using a modified x-ray collimator or using an attached collimator shutter as described later.

Figure 5:
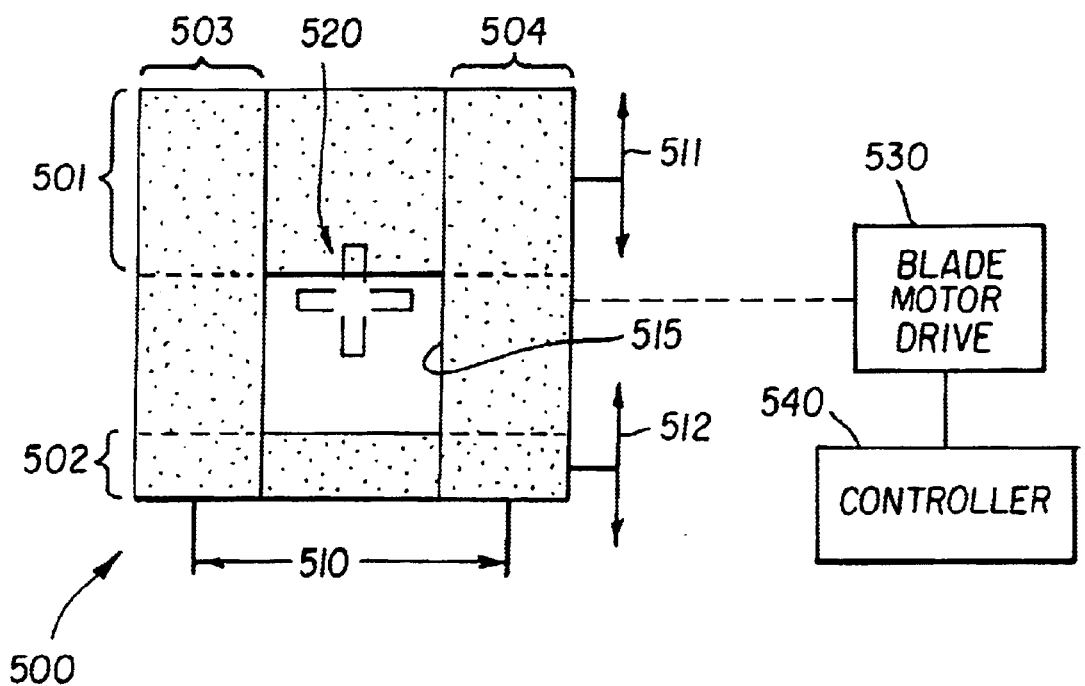
FIG. 5 is a diagrammatic view of a collimator according to the invention that allows the top blade and the bottom blade to move in the same direction.

Additional features need to be added to the conventional collimator in order to make it suitable for the present invention. FIG. 5 shows one of the preferred embodiments, where the top blade 501 of collimator 500 and the bottom blade 502 not only can move synchronously in opposite directions for adjusting the size of the aperture, the two blades can also move synchronously in the same direction to adjust the location of the aperture. The design of the left blade 503 and the right blade 504 does not change. In a different embodiment of the present invention, blade 501 and blade 503 can move independently in their respective directions 511, 512 to a desired exposure position. Arrow 520 indicates the exposure field center cross marker. For any embodiment of the present invention, the top blade 501 and the bottom blade 502 must track the DR detector for imaging partial regions as shown in FIG. 3. The blades can be motor-driven by blade motor drive 530 by the controlling computer 540 for automatic tracking of the detector position. The digital images sequentially taken are then stitched together to form a single radiographic image of a body part.

A collimator shutter can also be used with the conventional collimator to fulfill the requirement for DR imaging of long body parts. Prior to the first x-ray exposure, the collimator is configured to the desired exam length of the patient. This setup would be equivalent to the configuration that would be used if an extended length screen-film image were to be acquired. Second, a special shutter is placed in front of or inside the collimator to selectively allow the x-rays to reach the patient. A simple embodiment of the shutter is a flat sheet of x-ray opaque material with at least one opening. The opening can be any shape but in the preferred embodiment the shutter opening would be rectangular or square because the sharp and straight edges facilitate stitching of the acquired partial images. X-rays emitted from the x-ray tube pass through the opening unattenuated but are largely blocked by the shutter elsewhere. The location of the shutter is adjustable so that the opening can be adapted to match the DR detector position. The shutter can be implemented in a number of ways, such as a vertical translation type, a rotation type, or a horizontal translation type etc.

Figure 6A:
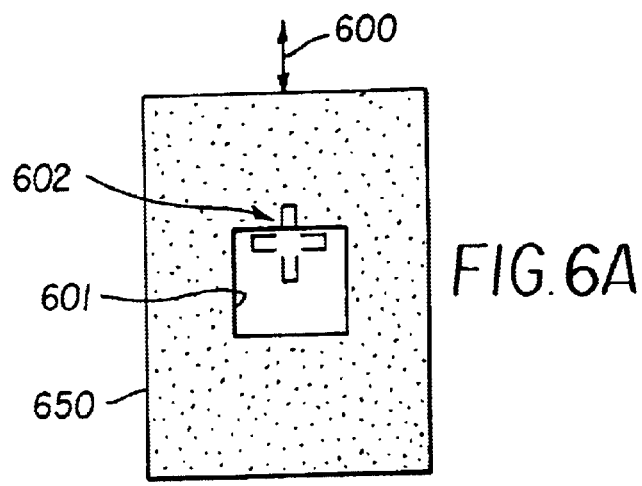
FIGS. 6A, 6B and 6C are diagrammatic views showing several collimation shutters: vertical translation type, rotation type, and the horizontal translation type useful in the present invention.
Figure 6B:
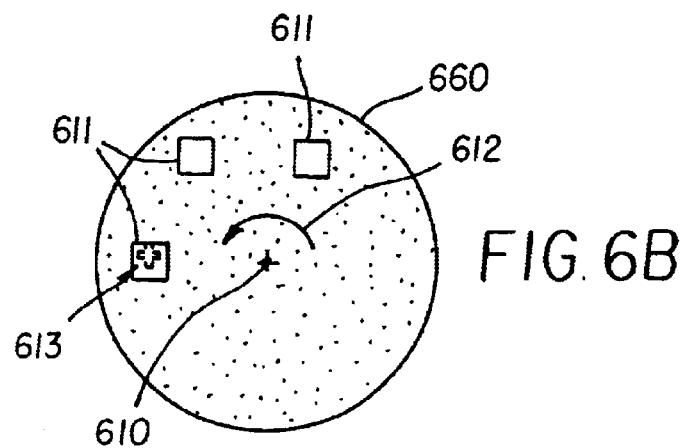
Figure 6C:
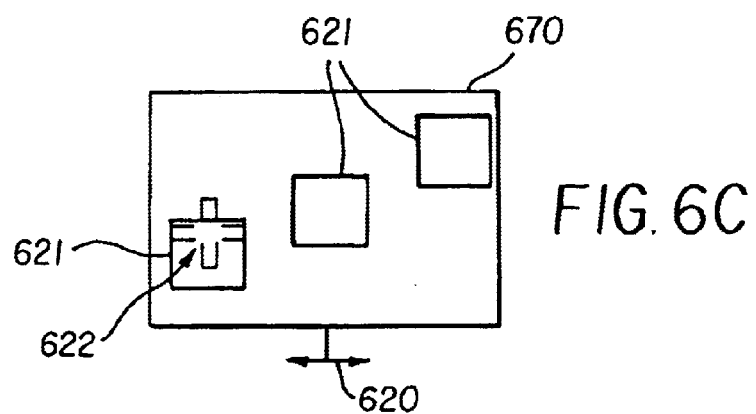

As shown in FIG. 6A, the vertical shutter 650 makes use of one fixed opening 601. The shutter 650 moves in front of the collimator up and down around the field center cross marker 602 in the direction of arrow 600. The size of the opening 601 can be designed such that the x-ray coverage though the opening is just sufficient to expose the DR detector. The rotation type shutter 660 of FIG. 6B has two or more circumferentially arrayed square openings 611 and can rotate around an axis 610 in the direction of arrow 612. The location of the openings 611 are designed such that as an individual opening 611 is rotated into the x-ray beam, the x-rays that pass through the opening expose the DR detector at a new location. The horizontal shutter 670 of FIG. 6C also has two or more diagonally arrayed openings 621. The entire shutter 670 is moved in the horizontal direction as indicated by arrow 620. Each opening 621 in the shutter permits the x-rays to expose the detector at a new location. The shutters can also be motor-driven and computer controlled for automatic tracking of the detector position (see FIG. 5).

Although the invention has been described as used in radiographic imaging of elongated body parts of a human patient, it will be understood that the present invention can also be used to radiographically image other elongated objects, such as manufactured objects, other biological objects, etc. The collimator or shutter can be made of any x-ray opaque material such as lead, aluminum, copper, etc.

The invention has been described in detail with particular reference to certain preferred embodiments thereof, but it will be understood that variations and modifications can be effected within the spirit and scope of the invention.

PARTS LIST 100 patient
101 x-ray tube and collimator
102 x-ray coverage
103 screen-film
200 patient
201 x-ray tube and collimator at a first location
202 x-ray coverage at a first location
203 DR detector at a first location
206 x-ray tube and collimator at a second location
207 x-ray coverage at a second location
208 DR detector at a second location
210 moving axis of x-ray tube and collimator from a first location to a second location
211 moving axis of DR detector from a fist location to a second location
300 patient
301 x-ray tube and collimator
302 x-ray coverage at a first detector location - A
303 DR detector
305 x-ray coverage at a second detector location - B
311 moving axis of DR detector from a first location to a second location
400 collimator
401 top blade
402 bottom blade
403 left blade
404 right blade -continued

PARTS LIST

| | |
|---|---|
| 410 | moving direction of left blade and right blade |
| 411 | moving direction of top blade and bottom blade |
| 420 | field center cross marker |
| 450 | opening |
| 500 | collimator |
| 501 | top blade |
| 502 | bottom blade |
| 503 | left blade |
| 504 | right blade |
| 510 | moving direction of left blade and right blade |
| 511 | moving direction of top blade |
| 512 | moving direction of bottom blade |
| 520 | field center cross marker |
| 530 | blade motor drive |
| 540 | controller |
| 600 | collimation shutter moving direction |
| 601 | square opening in collimation shutter |
| 602 | field center cross marker |
| 610 | collimation shutter rotation axial |
| 611 | square openings in collimation shutter |
| 612 | collimation shutter rotation direction |
| 613 | field center cross marker |
| 620 | collimation shutter moving direction |
| 621 | square openings in collimation shutter |
| 622 | field center cross marker |
| 650 | vertical shutter |
| 660 | rotation type shutter |
| 670 | horizontal shutter |

What is claimed is:

1. A method for acquiring a radiographic image of an elongated object, comprising:

positioning an elongated object between a source of x-rays and a digital image capture device having an imaging dimension which is less than a like dimension of said elongated object;

wherein said image source is stationary and said source projects an x-ray pattern which encompasses said elongated object;

moving said digital image capture device in a direction parallel to said known imaging dimension to sequential contiguous stationary positions to acquire a sequence of radiographic images of said elongated object; and moving an assembly of x-ray opaque material which is positioned between said source of x-rays and said elongated object, and which has an opening for allowing passage of x-rays, such that said opening is synchronized with the movement of said digital image capture device to facilitate acquisition of said sequence of radiographic images at said stationary positions.

2. The method of claim 1 wherein said digital image capture device includes a flat panel solid state digital image detector which is moved in said parallel direction.

3. The method of claim 1 wherein said assembly has blades which are adjustable along said parallel direction to form said opening.

4. The method of claim 1 wherein said assembly includes a member of x-ray opaque material which has a fixed opening; and wherein said member is movable in a vertical direction in synchronism with said movement of said digital image capture device so that said opening is aligned with said device at said sequential positions of said device.

5. The method of claim 1 wherein said assembly includes a member of x-ray opaque material which has a plurality of fixed openings which are arrayed diagonally; and wherein said member is movable in a horizontal direction in synchronism with the movement of said digital image capture device so that at each of said sequential positions of said device one of said fixed openings in aligned with said device.

6. The method of claim 1 wherein said assembly includes a member of x-ray opaque material which has a plurality of fixed openings which are arrayed circumferentially; and wherein said member is rotatable in synchronism with the movement of said digital image capture device so that at each of said sequential positions of said device, one of said fixed openings as aligned with said device.

7. A method for acquiring a radiographic image of an elongated body part, comprising:

positioning an elongated human body part between a source of x-rays and a digital image capture device having an imaging dimension which is less than a like dimension of said elongated body part;

wherein said image source is stationary and said source projects an x-ray pattern which encompasses said elongated body part;

moving said digital image capture device in a direction parallel to said known imaging dimension to sequential contiguous stationary positions to acquire a sequence of radiographic images of said elongated body part; and moving an assembly of x-ray opaque material which is positioned between said source of x-rays and said elongated body part, and which has an opening for allowing passage of x-rays, such that said opening is synchronized with the movement of said digital image capture device to facilitate acquisition of said sequence of radiographic images at said stationary positions.

8. The method of claim 7 wherein said digital image capture device includes a flat panel solid state digital image detector which is moved in said parallel direction.

9. The method of claim 7 wherein said assembly has blades which are adjustable along said parallel direction to form said opening.

10. The method of claim 7 wherein said assembly includes a member of x-ray opaque material which as a fixed opening; and wherein said member is movable in a vertical direction in synchronism with said movement of said digital image capture device so that said opening is aligned with said device at said sequential positions of said device.

11. The method of claim 7 wherein said assembly includes a member of x-ray opaque material which has a plurality of fixed openings which are arrayed diagonally; and wherein said member is movable in a horizontal direction in synchronism with the movement of said digital image capture device so that each of said sequential positions of said device one of said fixed openings is aligned with said device.

12. The method of claim 7 where said assembly includes a member of x-ray opaque material which has a plurality of fixed openings which are arrayed circumferentially; and wherein said member is rotatable in synchronism with the movement of said digital image capture device so that at each of said sequential positions of said device, one of said fixed openings is aligned with said device.

13. In a radiographic imaging system including a source of x-rays and an adjustable collimator associated with said source of x-rays for limiting the size of the x-ray beam projected to an object to be x-rayed, a shutter comprising;

a blade of x-ray opaque material having a fixed opening, said blade positioned contiguous to said collimator; and a blade drive for moving said blade in a vertical direction to position said opening in sequential, contiguous, stationary positions to control exposure of said object along said vertical direction.

14. In a radiographic imaging system including a source of x-rays and an adjustable collimator associated with said source of x-rays for limiting the size of the x-ray beam projected to an object to be x-rayed, a shutter comprising;
- a blade of x-ray opaque material having a plurality of fixed openings which are arrayed diagonally, said blade being positioned contiguous to said collimator; and
- a blade drive for moving said blade in a horizontal direction to position said diagonal array of openings in sequential, contiguous, stationary positions to control exposure of said object along a vertical direction.

15. In a radiographic imaging system including a source of x-rays and an adjustable collimator associated with said source of x-rays for limiting the size of the x-ray beam projected to an object to be x-rayed, a shutter comprising;
- a blade of x-ray opaque material having a plurality of fixed openings which are arrayed circumferentially, said blade being positioned contiguous to said collimator; and
- a blade drive for moving said blade in a rotational direction to position said circumferential, said blade being positioned contiguous to said collimator; and
- a blade drive for moving said blade in a rotational direction to position said circumferential array of openings in sequential, contiguous, stationary positions to control exposure of said object along a vertical direction.

* * * * *